United States Patent
Laas et al.

(10) Patent No.: US 7,098,289 B2
(45) Date of Patent: *Aug. 29, 2006

(54) ISOCYANATES CONTAINING URETDIONE GROUPS

(75) Inventors: Hans-Josef Laas, Bergisch Gladbach (DE); Reinhard Halpaap, Odenthal (DE); Frank Richter, Leverkusen (DE); Jürgen Köcher, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 180 days.

This patent is subject to a terminal disclaimer.

(21) Appl. No.: 10/613,457

(22) Filed: Jul. 3, 2003

(65) Prior Publication Data

US 2004/0049028 A1    Mar. 11, 2004

(30) Foreign Application Priority Data

| Jul. 4, 2002 | (DE) | 102 30 063 |
|---|---|---|
| Sep. 17, 2002 | (DE) | 102 43 029 |
| Sep. 17, 2002 | (DE) | 102 43 030 |

(51) Int. Cl.
   *C08G 18/20* (2006.01)

(52) U.S. Cl. .................... 528/52; 528/73; 540/202

(58) Field of Classification Search .......... 528/52, 528/73; 540/202
   See application file for complete search history.

(56) References Cited

U.S. PATENT DOCUMENTS

| 4,483,798 A | 11/1984 | Disteldorf et al. ...... 260/239 A |
|---|---|---|
| 4,595,534 A | 6/1986 | Scholl .................. 260/239 |
| 4,912,210 A | 3/1990 | Disteldorf et al. ........ 540/202 |
| 4,929,724 A | 5/1990 | Engbert et al. .......... 540/202 |
| 5,315,004 A * | 5/1994 | Goldstein et al. ........ 540/202 |
| 5,329,003 A | 7/1994 | Bruchmann ............ 540/202 |
| 5,621,064 A | 4/1997 | Laas et al. .............. 528/60 |
| 6,043,332 A | 3/2000 | Laas et al. .............. 528/51 |
| 2002/0095019 A1 | 7/2002 | Gras ................... 528/73 |

FOREIGN PATENT DOCUMENTS

EP    0 735 027    9/1997

OTHER PUBLICATIONS

J. prakt. Chem., 336, (month unavailable) 1994, pp. 185-200, Hans Josef Laas, Reinhard Halpaap und Josef Pedain, Zur Synthese aliphatischer Polyisocyanate—Lackpoly-Isocyanate mit Biuret-, Isocyanurat- oder Uretdionstruktur.

Justus Liebigs Annanlen der Chemie, vol. 562, (month unavailable) 1949, pp. 75-136, Von Werner Siefken "Mono- und Polyisocyanate".

* cited by examiner

*Primary Examiner*—Rachel Gorr
(74) *Attorney, Agent, or Firm*—Joseph C. Gil

(57) ABSTRACT

The invention relates to novel compounds containing uretdione groups, to a process for preparing them by dimerizing aliphatic and/or cycloaliphatic isocyanates containing exclusively secondary and/or tertiary isocyanate groups and also to the use of uretdione polyisocyanates obtainable by this process from diisocyanates containing exclusively secondary and/or tertiary isocyanate groups as a starting component for polyurethane polymers, in particular as an isocyanate component in the preparation of uretdione powder coating crosslinkers.

6 Claims, No Drawings

ISOCYANATES CONTAINING URETDIONE GROUPS

CROSS REFERENCE TO RELATED PATENT APPLICATION

The present patent application claims the right of priority under 35 U.S.C. §119 (a)–(d) of German Patent Application No. 102 43 030.6, filed Sep. 17, 2002.

FIELD OF THE INVENTION

The invention relates to novel compounds containing uretdione groups, to a process for preparing them by dimerizing aliphatic and/or cycloaliphatic isocyanates containing exclusively secondarily and/or tertiarily attached ("secondary and/or tertiary") isocyanate groups and also to the use of uretdione polyisocyanates obtainable by this process from diisocyanates containing exclusively secondary and/or tertiary isocyanate groups as a starting component for polyurethane polymers, and in particular as an isocyanate component in the preparation of uretdione powder coating crosslinkers.

BACKGROUND OF THE INVENTION

The preparation of polyisocyanates with uretdione structure by catalytic dimerization and optionally simultaneous trimerization of monomeric aliphatic or cycloaliphatic diisocyanates is known. A comprehensive overview of the industrially relevant dimerization processes of the prior art and of the catalysts and catalyst systems employed therein is in J. prakt. Chem. 336 (1994) 185–200.

Among the lightfast uretdione polyisocyanates there is great interest in the linear dimers, i.e. isocyanurate-group-free dimers, of cycloaliphatic diisocyanates in particular. These constitute preferred starting compounds in the preparation of blocking-agent-free polyurethane (PU) powder coating crosslinkers (e.g. EP-A 45 996, EP-A 639 598 or EP-A 669 353).

Whereas for the linear catalytic dimerization of aliphatic and/or cycloaliphatic diisocyanates containing at least one primarily attached ("primary") isocyanate group, such as 1,6-diisocyanatohexane (HDI) or 1-isocyanato-3,3,5-trimethyl-5-isocyanatomethylcyclohexane (isophorone diisocyanate; IPDI), a variety of processes exist (e.g. EP-A 45 995, EP-A 317 744, EP-A 735 027 and EP-A 896 973), some of which are also employed on the industrial scale in the preparation of powder coating crosslinkers, there have to date been no disclosures of isocyanurate-group-free uretdione polyisocyanates formed from aliphatic and/or cycloaliphatic diisocyanates containing exclusively secondary and/or tertiary isocyanate groups. The activity of the customary dimerization catalysts with respect to such diisocyanates is either zero or so low that it is impossible to use them even in very high catalyst concentrations to prepare the corresponding dimers in anything other than a vanishingly small yield, if at all.

Although some of the cited publications on the catalytic dimerization of isocyanates, for example in EP-A 178 520, DE-A 34 20 114, EP-A 317 744 or EP-A 896 973, have mentioned, inter alia, diisocyanates such as 2,4'- and/or 4,4'-diisocyanatodicyclohexylmethane, 1,3- and/or 1,4-diisocyanatocyclohexane, 1,3-diisocyanatocyclobutane or 1,3-diisocyanato-2(4)-methylcyclohexane as possible starting compounds, there has never been any specific description of uretdione polyisocyanates formed from cycloaliphatic diisocyanates containing no primary isocyanate groups, owing to the lack of activity of the dimerization catalysts known to date.

It was therefore an object of the present invention to provide a novel process for preparing uretdione polyisocyanates from aliphatic and/or cycloaliphatic diisocyanates containing exclusively secondary and/or tertiary isocyanate groups which produces, using highly reactive and selective catalysts, products, ideally linear and preferably free of isocyanurate groups, such as are required as starting components for uretdione powder coating crosslinkers.

SUMMARY OF THE INVENTION

The present invention is directed to a compound containing uretdione groups, having a molar fraction of isocyanurate structures, based on the sum of uretdione groups and isocyanurate groups, of not more than 10% as well as a process for making said compounds.

The present invention is also directed to a polyurethane prepared by reacting the inventive compound containing uretdione groups in a polyaddition process.

The present invention is further directed to powder coating compositions that include the inventive compound containing uretdione groups.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about."

The present invention provides compounds containing uretdione groups, which are obtainable by dimerizing aliphatic and/or cycloaliphatic isocyanates containing exclusively secondary and/or tertiary isocyanate groups and have a molar fraction of isocyanurate structures, based on the sum of uretdione groups and isocyanurate groups, of not more than 10%.

The present invention also provides a process for dimerizing compounds containing exclusively secondary and/or tertiary isocyanate groups in the presence of saltlike oligomerization catalysts, which contain 1,2,3- and/or 1,2,4-triazolate structures in the anion.

The invention also provides for the use of uretdione polyisocyanates obtained by the above described process from diisocyanates containing exclusively secondary and/or tertiary isocyanate groups as starting components for polyurethane polymers, in particular as isocyanate components in the preparation of uretdione powder coating crosslinkers.

Starting compounds for the process of the invention are any aliphatic and/or cycloaliphatic monoisocyanates and diisocyanates containing exclusively secondary and/or tertiary isocyanate groups, which may be prepared by any methods, non-limiting examples being by phosgenation or by a phosgene-free route, as for example by urethane cleavage. The designation "aliphatic and/or cycloaliphatic" refers merely to the nature of the carbon atoms bearing isocyanate groups; in other words, the molecule may certainly contain aromatic structures as well. Suitable starting isocyanates are, for example, monoisocyanates, such as 2-isocyanatopropane, 2-isocyanato-2-methylpropane, isocyanatocyclohexane, 1-isocyanato-4-isopropenyl-1-methylcyclohexane, 4-(1-isocyanato-1-methylethyl)-1-methyl-1-cyclohexene, 1,3-dimethyl-5-isocyanatoadamantane or 1-(1- isocyanato-1-methylethyl)-3-isopropenylbenzene (TMI), or diisocyanates, such as 1,3- and/or 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1,8-diisocyanato-p-menthane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 4,4'-diisocyanatodicyclohexylmethane, 4,4'-diisocyanato-3,3'-dimethyldicyclohexylmethane, 4,4'-diisocyanato-3,3',5,5'-tetramethyldicyclohexylmethane, 1,3-diisocyanatoadamantane, 1,3-dimethyl-5,7-diisocyanatoadamantane, 1,3- and 1,4-bis(1-isocyanato-1-methylethyl)benzene (TMXDI), bis(4-(1-isocyanato-1-methylethyl)phenyl) carbonate, and any desired mixtures of such monoisocyanates and diisocyanates. There are further starting isocyanates containing exclusively secondary and/or tertiary isocyanate groups, which are likewise suitable, to be found, furthermore, in, for example, Justus Liebigs Annalen der Chemie Volume 562 (1949) pp. 75–136.

In an embodiment of the invention, the starting isocyanates for the process of the invention are diisocyanates of the specified kind. In a particular embodiment, the starting compounds are 4,4'-diisocyanatodicyclohexylmethane, 1,3- and/or 1,4-diisocyanatocyclohexane or TMXDI. An especially preferred starting isocyanate is 4,4'-diisocyanatodicyclohexylmethane.

Oligomerization catalysts employed in the process of the invention are any saltlike compounds containing 1,2,3-triazolate and/or 1,2,4-triazolate structures in the anion. Compounds containing the anion triazolate structures include, but are not limited to those of the general formulas (I) and/or (II)

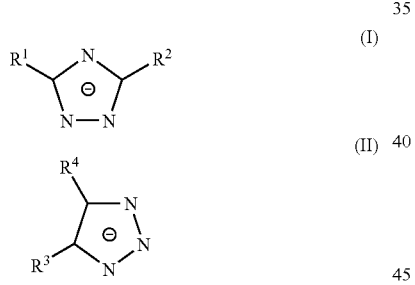

in which
R$^1$, R$^2$, R$^3$ and R$^4$ are identical or different radicals and are each selected from a hydrogen atom, a halogen atom selected from the fluorine, chlorine or bromine series or a nitro group, a saturated or unsaturated aliphatic or cycloaliphatic radical or an optionally substituted aromatic or araliphatic radical which can contain up to 20 carbon atoms and optionally up to 3 heteroatoms from the oxygen, sulphur and nitrogen series and can be optionally substituted by halogen atoms or nitro groups, and where
R$^3$ and R$^4$ in formula (II) together with the carbon atoms of the 1,2,3-triazolate five-membered ring can also form fused rings having 3 to 6 carbon atoms.

In an embodiment of the invention, the oligomerization catalysts include those containing in the anion triazolate structures of the general formula (I) in which
R$^1$ and R$^2$ are identical or different radicals and are each selected from a hydrogen atom, a halogen atom from the fluorine, chlorine or bromine series or a nitro group, a saturated aliphatic or cycloaliphatic radical or an optionally substituted aromatic or araliphatic radical which can contain up to 12 carbon atoms and optionally up to 3 heteroatoms from the oxygen, sulphur and nitrogen series and can optionally be substituted by halogen atoms or nitro groups.

In a further embodiment of the invention, the oligomerization catalysts include those containing in the anion triazolate structures of the general formula (II) in which
R$^3$ and R$^4$ are identical or different radicals and are each selected from a hydrogen atom, a halogen atom from the fluorine, chlorine or bromine series or a nitro group, a saturated or unsaturated aliphatic or cycloaliphatic radical or an optionally substituted aromatic or araliphatic radical which can contain up to 12 carbon atoms and optionally up to 3 heteroatoms from the oxygen, sulphur and nitrogen series and can optionally be substituted by halogen atoms or nitro groups and together with the carbon atoms of the 1,2,3-triazolate five-membered ring can also form fused rings having 3 to 6 carbon atoms.

In a particular embodiment of the invention, the oligomerization catalysts for the process of the invention include salts of 1,2,4-triazole, of 1,2,3-triazole and/or of 1,2,3-benzotriazole.

As counterions to the catalytically active triazolate anions the catalysts for use in accordance with the invention can contain any desired cations. Mention may be made here by way of example of alkali metal cations such as Li$^+$, Na$^+$ and K$^+$, alkaline earth metal cations such as Mg$^{2+}$ and Ca$^{2+}$, and ammonium or phosphonium cations, of the general formula (III),

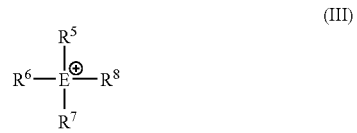

in which E is nitrogen or phosphorus,
R$^5$, R$^6$, R$^7$ and R$^8$ are identical or different radicals and are each selected from a hydrogen atom, a saturated or unsaturated aliphatic or cycloaliphatic radical or an optionally substituted aromatic or araliphatic radical which can contain up to 24 carbon atoms and optionally up to 3 heteroatoms from the oxygen, sulphur and nitrogen series and can optionally be substituted by halogen atoms or hydroxyl groups, and where
R$^8$ can also be a radical of the formula (IV)

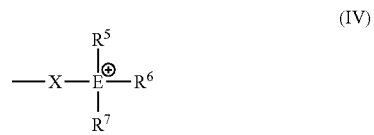

in which
X is a divalent, optionally substituted, aliphatic, cycloaliphatic, araliphatic or aromatic radical having up to 12 carbon atoms and
R$^5$, R$^6$, R$^7$ and E are as defined above.

In an embodiment of the invention, the cations are alkali metal ions or monovalent ammonium or phosphonium cations of the general formula (III) in which E is nitrogen or phosphorus and $R^5$, $R^6$, $R^7$ and $R^8$ are identical or different radicals and are each selected from a saturated aliphatic or cycloaliphatic radical or an optionally substituted aromatic or araliphatic radical having up to 18 carbon atoms.

The saltlike compounds used as oligomerization catalysts in the process of the invention are in some cases available commercially, in the form of their sodium salts, for example, and otherwise are readily obtainable by customary laboratory methods.

In the process of the invention these catalysts are employed generally in amounts of from 0.01 to 3% by weight, and in some cases from 0.1 to 2% by weight, based on the amount of isocyanate employed. They can be added to the reaction mixture in bulk; optionally, however, the catalysts may also be used in solution in a suitable organic solvent. The degree of dilution of the catalyst solutions may in this case be chosen freely within a very broad range. Catalytically active solutions are those with a concentration of or above 0.01% by weight Non-limiting examples of suitable catalyst solvents are solvents which are inert towards isocyanate groups, such as hexane, toluene, xylene, chlorobenzene, ethyl acetate, butyl acetate, diethylene glycol dimethyl ether, dipropylene glycol dimethyl ether, ethylene glycol monomethyl or monoethyl ether acetate, diethylene glycol-ethyl and butyl ether acetate, propylene glycol monomethyl ether acetate, 1-methoxyprop-2-yl acetate, 3-methoxy-n-butyl acetate, propylene glycol diacetate, acetone, methyl ethyl ketone, methyl isobutyl ketone, cyclohexanone, lactones such as β-propiolactone, γ-butyrolactone, ε-caprolactone and ε-methyl caprolactone, for example, but also solvents such as N-methylpyrrolidone and N-methylcaprolactam, 1,2-propylene carbonate, methylene chloride, dimethyl sulphoxide, triethyl phosphate or any mixtures of such solvents.

If catalyst solvents are employed at all in the process of the invention, they are suitably those which carry isocyanate-reactive groups and are incorporated in the reaction product. Examples of such solvents are monohydric or polyhydric simple alcohols, such as methanol, ethanol, n-propanol, isopropanol, n-butanol, n-hexanol, 2-ethyl-1-hexanol, ethylene glycol, propylene glycol, the isomeric butanediols, 2-ethyl-1,3-hexanediol or glycerol; ether alcohols, such as 1-methoxy-2-propanol, 3-ethyl-3-hydroxymethyloxetane, tetrahydrofurfuryl alcohol, ethylene glycol monomethyl ether, ethylene glycol monoethyl ether, ethylene glycol monobutyl ether diethylene glycol monomethyl ether, diethylene glycol monoethyl ether, diethylene glycol monobutyl ether, diethylene glycol, dipropylene glycol or else liquid higher-molecular-mass polyethylene glycols, polypropylene glycols, mixed polyethylene/polypropylene glycols and also the monoalkyl ethers thereof; ester alcohols, such as ethylene glycol monoacetate, propylene glycol monolaurate, glyceryl monoacetate and diacetate, glyceryl monobutyrate or 2,2,4-trimethyl-1,3-pentanediol monoisobutyrate; unsaturated alcohols such as allyl alcohol, 1,1-dimethyl allyl alcohol or oleyl alcohol; araliphatic alcohols such as benzyl alcohol; N-monosubstituted amides, such as N-methylformamide, N-methylacetamide, cyanoacetamide or 2-pyrrolidinone, for example, or any mixtures of such solvents.

If desired, especially when reacting diisocyanates, the oligomerization reaction in the process of the invention is terminated at the desired degree of conversion—for example, when from 10 to 60% of the isocyanate groups originally present in the starting mixture have reacted—with the aid of suitable catalyst poisons. Examples of such catalyst poisons are inorganic acids such as hydrochloric acid, phosphorous acid or phosphoric acid, acid chlorides such as acetyl chloride, benzoyl chloride or isophthaloyl dichloride, sulphonic acids and sulphonic esters, such as methanesulphonic acid, p-toluenesulphonic acid, trifluoromethanesulphonic acid, perfluorobutanesulphonic acid, dodecylbenzenesulphonic acid, methyl p-toluenesulphonate and ethyl p-toluenesulphonate, monoalkyl and dialkyl phosphates such as monotridecyl phosphate, dibutyl phosphate and dioctyl phosphate, but also silylated acids, such as trimethylsilyl methanesulphonate, trimethylsilyl trifluoromethanesulphonate, tris(trimethylsilyl) phosphate and diethyl trimethylsilyl phosphate.

The amount of the catalyst poison needed to stop the reaction is guided by the molar amount of the catalyst used; generally speaking, an equivalent molar amount of the stopping agent, based on the oligomerization catalyst used to start with, is employed. However, taking into account possible catalyst losses during the reaction, it may be sufficient to stop the reaction using just 20 to 80 mol % of the catalyst poison, based on the molar amount of catalyst originally employed.

The aforementioned catalyst poisons may be used either in bulk or in solution in a suitable organic solvent. Suitable solvents are, for example, the solvents already described above as possible catalyst solvents, or mixtures thereof. The degree of dilution can be chosen freely within a very broad range: suitable solutions, for example, are those with a concentration of or above 10% by weight.

In addition to the organic solvents mentioned, the above mentioned starting isocyanates containing exclusively secondary and/or tertiary isocyanate groups may also act as solvents for the catalyst poisons in the process of the invention provided that they are sufficiently inert towards isocyanate groups, and so allow storage-stable solutions to be prepared.

In the process of the invention it is also possible if desired to use additives customary in polyurethane chemistry as stabilizers. Such additives include, but are not limited phenolic antioxidants, such as 2,6-di-tert-butyl-4-methylphenol, 2,4,6-tri-tert-butylphenol and 3,5-di-tert-butyl-4-hydroxyanisole, for example, or phosphite stabilizers trisubstituted by alkyl and/or aryl radicals, such as triphenyl phosphite, tris(nonylphenyl) phosphite, diphenyl isooctyl phosphite, diphenyl isodecyl phosphite, diisodecyl phenyl phosphite, diisooctyl octylphenyl phosphite, phenyl neopentyl glycol phosphite, 2,4,6-tri-tert-butylphenyl 2-butyl-2-ethyl-1,3-propanediol phosphite, triisodecyl phosphite, trilauryl phosphite, tris(tridecyl) phosphite, diisodecyl pentaerythritol diphosphite, distearyl pentaerythritol diphosphite, bis-(2,4-di-tert-butylphenyl) pentaerythritol diphosphite and tetraphenyl dipropylene-glycol diphosphite or any mixtures of such additives.

If these additives are used at all, they are added to the reaction mixture in an amount of up to 5% by weight, in some cases up to 3% by weight, based on the amount of starting isocyanates employed.

In one particular embodiment of the process of the invention, additives of the type specified which are liquid at room temperature, preferably the liquid phosphite stabilizers mentioned, serve as solvents for the catalysts and/or catalyst poisons employed.

Apart from any catalyst solvents and/or stopper solvents which may be used, the process of the invention is usually conducted in bulk. However it can also be carried out if desired in the presence of further amounts of solvents which are inert towards isocyanate groups. Suitable examples include, but are not limited to the non-reactive solvents already described above as possible catalyst solvents, or any desired mixtures of these solvents, which can be used optionally in an amount of up to 80% by weight, based on the total amount of starting isocyanates and added solvent.

To carry out the process of the invention the stated starting compounds containing exclusively secondary and/or tertiary isocyanate groups are charged optionally under inert gas such as nitrogen, for example, optionally in the presence of a suitable solvent and optionally of a stabilizer of the type specified to a vessel at a temperature of from 0 to 100° C., in some cases from 20 to 60° C. Then an oligomerization catalyst or a solution of an oligomerization catalyst of the above mentioned type is added in the amount indicated above and the reaction temperature is adjusted where appropriate by a suitable measure (heating or cooling) to a temperature of from 20 to 100° C., in some cases 25 to 80° C. The catalyst can be added in one or more portions or else continuously, using a suitable metering pump, as a non-limiting example, over the entire reaction time. The reaction can optionally be ended at a target degree of oligomerization—as a non-limiting example, on reaching a degree of oligomerization of from 10 to 60%, in some cases from 10 to 40%—by addition of a catalyst poison of the type exemplified and optionally subsequent brief heating of the reaction mixture at, as a non-limiting example, a temperature lying above 80° C. By "degree of oligomerization" is meant here the percentage of the isocyanate groups originally present in the starting mixture (and corresponding to 100%) which is consumed during the reaction according to the invention (in particular by dimerization, additionally with trimerization and, in the case where the catalyst solvents described, for example alcoholic catalyst solvents, are used as well, by reaction with isocyanate groups involving urethanization, for example). The stated degree of oligomerization is generally reached after a reaction time of from 30 minutes to 8 hours, in some cases from 1 to 6 hours.

The reaction mixture is freed subsequently by thin-film distillation at pressures from 0.001 to 20 mbar, in some cases from 0.01 to 5 mbar, under conditions as gentle as possible, non-limiting examples being at a temperature of from 120 to 220° C., in some cases from 140 to 190° C., from volatile constituents (excess monomeric starting isocyanates and any non-reactive solvents and stabilizers used).

In another embodiment of the process of the invention the stated volatile constituents are separated off from the oligomerization product by extraction with suitable solvents which are inert towards isocyanate groups, non-limiting examples being aliphatic or cycloaliphatic hydrocarbons such as pentane, hexane, heptane, cyclopentane or cyclohexane.

In this way, depending on the nature of the starting isocyanates chosen, pale-coloured or almost colourless products are obtained which contain uretdione groups and whose isocyanate group content, depending on the degree of oligomerization, is up to 25.4% by weight, in some cases up to 23.9% by weight, or, when using exclusively diisocyanates as starting compounds, from 11.2 to 25.4% by weight, in some cases from 12.8 to 23.9% by weight, and which contain less than 5% by weight, in some cases less than 2% by weight, and in other cases less than 1% by weight, of monomeric starting isocyanates. The molar fraction of isocyanurate structures in the process products of the invention, based on the sum of uretdione groups and isocyanurate groups, is preferably not more than 10%, more preferably not more than 8% and very preferably not more than 5%.

The distillates obtained, which in addition to unreacted monomeric starting isocyanates contain any solvents and stabilizers used and also, in the absence of a catalyst poison, may contain active catalyst, can be readily used for further oligomerization.

With the process of the invention it is possible if desired, following partial catalytic polymerization and termination of the reaction at the target degree of oligomerization by addition of a catalyst poison, to dispense with the removal of the excess, unreacted starting diisocyanate. In this case the process products obtained are pale-coloured solutions of compounds containing uretdione groups in up to 70% by weight of monomeric starting isocyanate.

The process of the invention permits for the first time the dimerization of secondary and/or tertiary isocyanate groups in a simple way using very low catalyst concentrations and within very short reaction times.

The uretdione polyisocyanates obtainable by this process from diisocyanates containing exclusively secondary and/or tertiary isocyanate groups, or solutions of the said polyisocyanates in monomeric starting diisocyanates, constitute valuable starting materials for the preparation of polyurethane polymers by the polyaddition process, preferably for the preparation of one-component or two-component polyurethane coating materials. In this context they can also be used as crosslinker components for one-component baking varnishes, in a form in which they have been blocked with blocking agents known per se from polyurethane chemistry. Non-limiting examples of suitable blocking agents are the following compounds known from polyurethane chemistry as blocking agents for isocyanate groups: oximes, such as acetone oxime, butanone oxime and cyclohexanone oxime, for example, lactams, such as ε-caprolactam, C—H-acidic compounds, such as diethyl malonate and acetoacetates, N-heterocycles, such as 1,2,4-triazole, dimethyl-1,2,4-triazole, 3,5-dimethylpyrazole and imidazole, and any mixtures of these blockings agents.

The uretdione polyisocyanates obtainable by the process of the invention from diisocyanates containing exclusively secondary and/or tertiary isocyanate groups are particularly suitable as starting components for the preparation of uretdione powder coating crosslinkers.

EXAMPLES

The examples below serve for further illustration of the invention. The term "degree of oligomerization" denotes the percentage of the isocyanate groups originally present in the starting mixture (which correspond to 100%) consumed during the reaction according to the invention—for example, consumed by dimerization and trimerization.

Preparation of the Catalysts

Catalyst 1: Sodium 1,2,4-triazolate

A three-necked-flask stirring apparatus with mechanical stirrer, internal thermometer and reflux condenser was charged under dry nitrogen with 200 ml of dry methanol and 45 ml of a 30% strength methanolic solution of sodium methoxide, corresponding to 0.25 mol of sodium methoxide. 17.4 g (0.25 mol) of 1,2,4-triazole was added thereto in portions at room temperature. After the end of addition of the 1,2,4-triazole the reaction mixture was stirred at reflux temperature for 4 h. The solvent was subsequently distilled off under reduced pressure and the oily residue which remained was admixed at room temperature with 200 ml of methylene chloride. The mixture was stirred at room temperature for 15 min and the precipitated solid product was filtered off. This gave 22.5 g of sodium 1,2–4-triazolate (yield: 98% of theory) in the form of a colourless powder. The product was pure according to its $^1$H-NMR spectrum and free of the 1,2,4-triazole used.

Catalyst 2: Sodium 1,2,3-triazolate 17.4 g (0.25 mol) of 1,2,3-triazole was reacted with an equivalent amount of methanolic sodium methoxide solution in 200 ml of methanol by the process described for catalyst 1. The reaction mixture was worked up as described above to give 22.4 g of sodium 1,2,3-triazolate (yield: 98% of theory) in the form of a virtually colourless powder. The product was pure according to its $^1$H-NMR spectrum and free from starting material.

Catalyst 3: Sodium Benzotriazolate 29.8. g (0.25 mol) of benzotriazole were reacted with an equivalent amount of methanolic sodium methoxide solution in 200 ml of methanol by the process described for catalyst 1. The reaction mixture was worked up as described above to give 34.2 g of sodium benzotriazolate (yield: 97% of theory) in the form of a virtually colourless powder. The product was pure according to its $^1$H-NMR spectrum and free from starting material.

Catalyst 4: Tetrabutylphosphonium 1,2,4-triazolate

A three-necked-flask stirring apparatus with mechanical stirrer, internal thermometer and reflux condenser was charged at room temperature under dry nitrogen with 18.0 g of a 30% strength methanolic sodium methoxide solution, corresponding to 0.1 mol of sodium methoxide. Over the course of 20 min, a solution of 6.9 g (0.1 mol) of 1,2,4-triazole in 20 ml of methanol was added dropwise, after which the reaction mixture was stirred for an hour and then, over the course of 20 min, 41.3 g (0.1 mol) of a 71.4% strength by weight solution of tetrabutylphosphonium chloride in isopropanol (Cyphos® 443P, Cytec Industries, Neuss) was added. The commencement of addition of the phosphonium salt was followed immediately by the onset of precipitation of sodium chloride. The reaction mixture was stirred for a further hour at room temperature and filtered and finally the filtrate was concentrated to a volume of about 50 ml on a rotary evaporator at a bath temperature of 40° C. and a pressure of about 1 mbar. The residue was filtered again to give 42.5 g of a clear, almost colourless solution of tetrabutylphosphonium 1,2,4-triazolate in a methanol/isopropanol mixture. The active catalyst content according to acidimetric titration with 0.1 N HCl against phenolphthalein was 73.0% by weight; the ratio of methanol to isopropanol was determined by gas chromatography (GC) as 25.4:74.6% (area %).

Catalyst 5: Methyltrioctylammonium 1,2,4-triazolate

Using the process described for catalyst 4, 6.9 g (0.1 mol) of 1,2,4-triazole in solution in 20 g of methanol were reacted first with 18.0 g (0.1 mol) of 30% strength methanolic sodium methoxide solution and then with 80.6 g of a 50% strength solution of methyltrioctylammonium chloride (Aliquat® 336, Cognis Deutschland GmbH & Co. KG, Düsseldorf) in methanol, corresponding to 0.1 mol of methyltrioctylammonium chloride. Filtration, removal of the solvent by rotary evaporator and further filtration gave 40.3 g of methyltrioctylammonium 1,2,4-triazolate as a clear, pale yellow liquid. The active catalyst content according to acidimetric titration with 0.1 N HCl was 92.3% by weight.

Catalyst 6: Trihexyltetradecylphosphonium 1,2,4-triazolate

A three-necked-flask stirring apparatus with mechanical stirrer, internal thermometer and reflux condenser was charged at room temperature under dry nitrogen with 180.0 g of a 30% strength methanolic sodium methoxide solution, corresponding to 1.0 mol of sodium methoxide. Over the course of 45 min a solution of 69 g (1.0 mol) of 1,2,4-triazole in 200 ml of methanol was added dropwise, and the reaction mixture was subsequently stirred for 12 hours. Then over the course of one hour a solution of 518 g (1.0 mol) of trihexyltetradecylphosphonium chloride (Cyphos® 3653P, Cytec Industries, Neuss) in 60 g of methanol was added dropwise. The beginning of addition of the phosphonium salt was followed immediately by the onset of sodium chloride precipitation. The reaction mixture was stirred overnight, the precipitated sodium chloride was filtered off and the solvent was subsequently distilled off in a commercially customary thin-film evaporator at a temperature of 50° C. and a pressure of about 0.3 mbar. The residue was filtered again to give 510 g (yield: 92.6% of theory) of trihexyltetradecylphosphonium 1,2,4-triazolate as a clear, almost colourless liquid having a viscosity of 570 mPas (23° C.) and a refractive index $n_D^{20}$ of 1.4821. The residual methanol content was 0.1% by weight.

Example 1

1000 g (3.82 mol) of 4,4'-diisocyanatodicyclohexylmethane were admixed at 30° C. under dry nitrogen and with stirring with a solution of 2 g (0.022 mol) of sodium 1,2,4-triazolate (catalyst 1) in 25 ml of dimethyl sulphoxide (DMSO), whereupon the temperature of the reaction mixture rose to 39° C. owing to the heat of reaction released. After a reaction time of 60 minutes, during which the exotherm subsided again, the NCO content of the reaction mixture had dropped to 26.3% by weight, corresponding to a degree of oligomerization of 15.6%. The catalyst was then deactivated by adding 4.6 g (0.022 mol) of dibutyl phosphate. The turbidity generated in this deactivation was removed by filtration and the clear, colourless reaction mixture was freed from volatile constituents (excess diisocyanate and catalyst solvent) at a temperature of 155° C. and a pressure of 0.2 mbar. This gave a colourless uretdione polyisocyanate having a free NCO group content of 14.1% by weight, a monomeric 4,4'-diisocyanatodicyclohexylmethane content of 0.4% by weight, a viscosity (according to DIN 53 018) of more than 200,000 mPas (23° C.) and a colour number (APHA), determined on a 10% strength by weight solution in methylene chloride, of 12. The molar ratio of uretdione structures to isocyanurate structures according to $^{13}$C-NMR spectroscopy was 98.4:1.6.

Example 2

1000 g (3.82 mol) of 4,4'-diisocyanatodicyclohexylmethane were admixed at 30° C. under dry nitrogen and with stirring with a solution of 2 g (0.022 mol) of sodium 1,2,3-triazolate (catalyst 2) in 25 ml of dimethyl sulphoxide (DMSO), whereupon the temperature of the reaction mixture rose to 39° C. owing to the heat of reaction released. After a reaction time of 60 minutes, during which the exotherm subsided again, the NCO content of the reaction mixture had dropped to 26.7% by weight, corresponding to a degree of oligomerization of 14.3%. The catalyst was then deactivated by adding 4.6 g (0.022 mol) of dibutyl phosphate and the reaction mixture was worked up as described in Example 1. This gave a colourless uretdione polyisocyanate of high viscosity having a free NCO group content of 14.1% by weight, a monomeric 4,4'-diisocyanatodicyclohexylmethane content of 0.5% by weight, and a colour number (APHA), determined on a 10% strength by weight solution in methylene chloride, of 14. The molar ratio of uretdione structures to isocyanurate structures according to $^{13}$C-NMR spectroscopy was 99.1:0.9.

Example 3

1000 g (3.82 mol) of 4,4'-diisocyanatodicyclohexylmethane were admixed at 30° C. under dry nitrogen and with stirring with a solution of 3.0 g (0.021 mol) of sodium benzotriazolate (catalyst 3) in 40 ml of dimethyl sulphoxide (DMSO), whereupon the temperature of the reaction mixture rose to 37° C. owing to the heat of reaction released. After a reaction time of 60 minutes, during which the exotherm subsided again, the NCO content of the reaction mixture had dropped to 26.5% by weight, corresponding to a degree of oligomerization of 13.6%. The catalyst was then deactivated by adding 4.4 g (0.021 mol) of dibutyl phosphate and the reaction mixture was worked up as described in Example 1. This gave a colourless uretdione polyisocyanate of high viscosity having a free NCO group content of 14.0% by weight, a monomeric 4,4'-diisocyanatodicyclohexylmethane content of 0.5% by weight, and a colour number (APHA), determined on a 10% strength by weight solution in methylene chloride, of 21. The molar ratio of uretdione structures to isocyanurate structures according to $^{13}$C-NMR spectroscopy was 96.4:3.6.

Example 4

1000 g (3.82 mol) of 4,4'-diisocyanatodicyclohexylmethane were admixed at 30° C. under dry nitrogen and with stirring with a solution of 2.3 g (5.1 mmol) of catalyst 4 (tetrabutylphosphonium 1,2,4-triazolate in methanol/isopropanol), whereupon the temperature of the reaction mixture rose to 42° C. owing to the heat of reaction released. After the exotherm has subsided the batch was recatalysed after 40 minutes with a further 2.3 g (5.1 mmol) of catalyst solution. After a reaction time of 1 hour 25 minutes in total, the NCO content of the reaction mixture had dropped to 26.5% by weight, corresponding to a degree of oligomerization of 13.6%. The catalyst was then deactivated by adding 2.15 g (10.2 mmol) of dibutyl phosphate and the reaction mixture was freed from excess diisocyanate as described in Example 1 by thin-film distillation. This gave a pale yellow uretdione polyisocyanate of high viscosity having a free NCO group content of 14.2% by weight, a monomeric 4,4'-diisocyanatodicyclohexylmethane content of 0.4% by weight, and a colour number (APHA), determined on a 10% strength by weight solution in methylene chloride, of 17. The molar ratio of uretdione structures to isocyanurate structures according to $^{13}$C-NMR spectroscopy was 97.2:2.8

Example 5

1000 g (3.82 mol) of 4,4'-diisocyanatodicyclohexylmethane were degassed under reduced pressure (2 mbar) for 1 hour, then blanketed with dry nitrogen and warmed to 30° C. With stirring, 8 g (0.02 mol) of catalyst 5 (methyltrioctylammonium 1,2,4-triazolate) were added, with the reaction mixture warming to 43° C. owing to the heat or reaction liberated. After a reaction time of 70 minutes, during which the exotherm subsided again, the NCO content of the reaction mixture was 26.6% by weight, corresponding to a degree of oligomerization of 16.2%. The catalyst was then deactivated by adding 4.2 g (0.2 mol) of dibutyl phosphate and the resultant clear, colourless mixture was freed from excess diisocyanate as described in Example 1 by thin-film distillation. This gave a virtually colourless uretdione polyisocyanate of high viscosity having a free NCO group content of 14.0% by weight, a monomeric 4,4'-diisocyanatodicyclohexylmethane content of 0.3% by weight, and a colour number (APHA), determined on a 10% strength by weight solution of methylene chloride, of 10. The molar ratio of uretdione structures to isocyanurate structures according to $^{13}$C-NMR spectroscopy was 99.3:0.7.

Example 6

1000 g (3.82 mol) of 4,4'-diisocyanatodicyclohexylmethane were degassed under reduced pressure (2 mbar) for 1 hour, then blanketed with dry nitrogen and warmed to 30° C. Subsequently, with stirring, 12 g (0.022 mol) of catalyst 6 (trihexyltetradecylphosphonium 1,2,4-triazolate) were added continuously over a reaction time of 3 hours, using a laboratory infusion pump (KDS 100, KD Scientific, Boston). After a subsequent stirring time of 30 min the NCO content of the reaction mixture was 26.2% by weight, corresponding to a degree of oligomerization of 17.1%. The catalyst was then deactivated by adding 4.6 g (0.022 mol) of dibutyl phosphate and the resultant clear, colourless mixture was freed from excess diisocyanate as described in Example 1 by thin-film distillation. This gave a virtually colourless uretdione polyisocyanate of high viscosity having a free NCO group content of 14.2% by weight, a monomeric 4,4'-diisocyanatodicyclohexylmethane content of 0.5% by weight, and a colour number (APHA), determined on a 10% strength by weight solution of methylene chloride, of 11. The product according to $^{13}$C-NMR spectroscopy contained exclusively uretdione groups. Isocyanurate structures were not detectable.

Comparative Example 1

In Accordance With EP-A 317 744

1000 g (3.82 mol) of 4,4'-diisocyanatodicyclohexylmethane were admixed at room temperature under dry nitrogen and with stirring with 20 g (2% by weight) of 4-dimethylaminopyridine (DMAP) catalyst. After 5 days the virtually colourless reaction mixture had an unchanged NCO content of 31.4% by weight. In the IR spectrum as well there was no indication of uretdione groups.

Comparative Example 2

In Accordance With EP-A 317 744

1000 g of 4,4'-diisocyanatodicyclohexylmethane were admixed as described in Comparative Example 1 with 20 g (2% by weight) of DMAP and then heated at 50° C. for 5 days. The pale yellow reaction mixture had an unchanged NCO content of 31.4% by weight. In the IR spectrum there was no indication of uretdione groups.

Comparative Example 3

In Accordance With EP-A 317 744

1000 g (3.82 mol) of 4,4'-diisocyanatodicyclohexylmethane were admixed at room temperature under dry nitrogen and with stirring with 100 g (10% by weight) of 4-dimethylaminopyridine (DMAP) catalyst. After 5 days the IR spectrum showed a very weakly pronounced band at 1760 cm$^{-1}$, which can be interpreted as an indication of the presence of small amounts of uretdione groups. The NCO content of the pale yellow reaction mixture had dropped from 29.0 to 28.6% by weight, corresponding to a degree of oligomerization of 1.4%.

Comparative Example 4

In Accordance With EP-A 45 995

1000 g (3.82 mol) of 4,4'-diisocyanatodicyclohexylmethane were admixed at room temperature under dry nitrogen and with stirring with 50 g (5% by weight) of hexamethylphosphoramide. After 5 days the virtually colourless reaction mixture had an unchanged NCO content of 31.3% by weight. In the IR spectrum there was no indication of uretdione groups.

The comparative examples show that the catalysts known from the literature for the highly selective dimerization of isocyanates, in contrast to the catalysts of the process of the invention, even in high concentrations have no activity with respect to secondary isocyanate groups or have only an extremely low activity which is completely inadequate for the industrial preparation of uretdione polyisocyanates.

Examples 7 and 8

In accordance with the process described in Example 6, 500 g each of 4,4'-diisocyanato-3,3'-dimethyldicyclohexylmethane (Example 7) and TMXDI (Example 8) were oligomerized in the presence of catalyst 6 at 30° C. The reaction mixtures were each stopped with an equimolar amount of dibutyl phosphate and then worked up by thin-film distillation. The table below shows the individual amounts of catalyst and stopper used (in each case in % by weight based on the amount of starting isocyanate employed), reaction times and characteristic data of the resins obtained after thin-film distillation.

| Example | 7 | 8 |
|---|---|---|
| Catalyst concentration [%] | 1.0 | 1.0 |
| Reaction time [h] | 3.0 | 3.0 |
| Subsequent stirring time [h] | 0.5 | 0.5 |
| Distillation temperature [° C.] | 160 | 160 |
| Degree of oligomerization [%] | 13.4 | 7.7 |
| NCO content [%] | 13.3 | 15.6 |
| Monomer content [%] | 0.6 | 0.5 |
| Colour number [APHA][a)] | 29 | 43 |
| IR; uretdione band [cm$^{-1}$] | 1759.4 | 1764.2 |
| Uretdione: isocyanurate [mol-%][b)] | 100:0 | 100:0 |

[a)]determined on a 10% strength by weight solution in methylene chloride
[b)]determined by $^{13}$C-NMR spectroscopy Example 9

100 g of cyclohexyl isocyanate were admixed at room temperature under dry nitrogen with 1% by weight of catalyst 6. After 24 h at room temperature the NCO content had dropped from an initial 33.6% by weight to 29.9% by weight, corresponding to a degree of oligomerization of 10.1%. According to the IR spectrum exclusively uretdione structures had formed (band at 1760.7 cm$^{-1}$), isocyanurate structures were not detectable.

Example 10

100 g of tert-butyl isocyanate were admixed at room temperature under dry nitrogen with 1% by weight of catalyst 6. After 24 h at room temperature the NCO content had dropped from an initial 42.0% by weight to 35.7% by weight, corresponding to a degree of oligomerization of 15.0%. According to the IR spectrum exclusively uretdione structures had formed (band at 1763.5 cm$^{-1}$); isocyanurate structures are not detectable.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for dimerizing compounds containing exclusively secondary and/or tertiary isocyanate groups comprising dimerizing said compounds in the presence of a saltlike oligomerization catalyst containing one or both of 1,2,3-triazolate structures and 1,2,4-triazolate structures in the anion of the catalyst.

2. The process according to claim 1, wherein the anion of the saltlike oligomerization catalyst contains one or both triazolate structures of the general formulas (I) and (II)

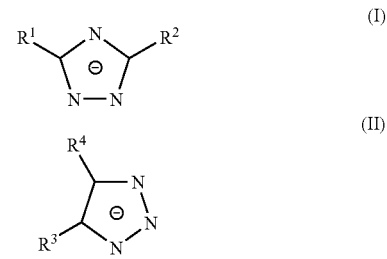

wherein
R$^1$,R$^2$,R$^3$ and R$^4$ are independently identical or different radicals selected from a hydrogen atom; a halogen atom selected from fluorine, chlorine and bromine; a nitro group; a saturated or unsaturated aliphatic or cycloaliphatic radical; an optionally substituted aromatic or araliphatic radical containing up to 20 carbon atoms and optionally up to 3 heteroatoms selected from oxygen, sulphur and nitrogen and optionally substituted by halogen atoms or nitro groups and where R$^3$ and R$^4$ in formula (II) together with the carbon atoms of the 1,2,3-triazolate five-membered ring also form optionally fused rings having 3 to 6 carbon atoms.

3. The process according to claim 2, wherein the anion of the saltlike oligomerization catalyst compound contains the triazolate structures of general formula (I), wherein R$^1$ and R$^2$ are identical or different radicals selected from a hydrogen atom; a halogen atom selected from fluorine, chlorine and bromine; a nitro group; a saturated aliphatic or cycloaliphatic radical or an optionally substituted aromatic or araliphatic radical containing up to 12 carbon atoms and optionally up to 3 heteroatoms selected from oxygen, sulphur and nitrogen and can optionally be substituted by halogen atoms or nitro groups.

4. The process according to claim 2, wherein the anion of the saltlike oligomerization catalyst compound contains the triazolate structure of general formula (II), wherein R$^3$ and R$^4$ are identical or different radicals selected from a hydrogen atom; a halogen atom selected from fluorine, chlorine and bromine; a nitro group; a saturated or unsaturated aliphatic or cycloaliphatic radical or an optionally substituted aromatic or araliphatic radical containing up to 12 carbon atoms and optionally up to 3 heteroatoms selected from oxygen, sulphur and nitrogen and can optionally be substituted by halogen atoms or nitro groups; and together with the carbon atoms of the 1,2,3-triazolate five-membered ring also form optionally fused rings having 3 to 6 carbon atoms.

5. The process according to claim 2, wherein the anion of the saltlike oligomerization catalyst comprises one or more salts of compounds selected from 1,2,4-triazole, 1,2,3-triazole and 1,2,3-benzotriazole, and mixtures thereof.

6. The process according to claim 5, wherein the oligomerization catalyst contain as cations one or more compounds selected from alkali metal ions, monovalent ammonium ions, and phosphonium cations of the general formula (III)

wherein

E is nitrogen or phosphorus, and $R^5$, $R^6$, $R^7$ and $R^8$ are identical or different radicals selected from saturated aliphatic or cycloaliphatic radicals and optionally substituted aromatic or araliphatic radical having up to 18 carbon atoms.

* * * * *